United States Patent [19]

Kelly

[11] Patent Number: 4,547,187

[45] Date of Patent: Oct. 15, 1985

[54] INFLATABLE CHOLANGIOCATH AND METHOD FOR CHOLANGIOGRAPHY THEREWITH

[75] Inventor: Thomas R. Kelly, Akron, Ohio

[73] Assignee: Thomas R. Kelly, M.D., Inc., Akron, Ohio

[21] Appl. No.: 492,134

[22] Filed: May 6, 1983

[51] Int. Cl.[4] ............................................. A61M 25/00
[52] U.S. Cl. ........................................ 604/49; 604/97; 604/284
[58] Field of Search .................................. 604/96–99, 604/101, 103, 284, 49; 128/656–658, 328

[56] References Cited

U.S. PATENT DOCUMENTS

| | | | |
|---|---|---|---|
| 3,392,722 | 7/1968 | Jorgensen | 604/284 X |
| 3,577,992 | 5/1971 | Merry et al. | 604/103 X |
| 4,154,244 | 5/1979 | Becker et al. | 604/96 |
| 4,178,932 | 12/1979 | Taylor | 604/103 |
| 4,230,119 | 10/1980 | Blum | 604/101 X |

OTHER PUBLICATIONS

American Castoscope Makers, Inc., Catalogue of Catheters and Accessories, 1960, p. 64.
"Just Another Patient with Gallstones? Don't You Believe It" *Nursing 79*, (Vol. 9, No. 10, Oct. 1979, pp. 26–33), Judy Bell.

*Primary Examiner*—Stephen C. Pellegrino
*Attorney, Agent, or Firm*—Renner, Kenner, Greive & Bobak Co.

[57] ABSTRACT

An inflatable cholangiocath (10) includes an elongate shaft (11) having a proximal and a distal end (12,14), a second shaft (15) carried at the distal end and having left and right branches (16,18) adapted to be inserted into an incised duct of a patient and a central drainage lumen (24) extending from the proximal end, through the elongate shaft, and out the left and right branches, balloon means (30) encompassing a portion of the distal end and the left and right branches, the balloon means being closed to the central drainage lumen and, means for selectively inflating and deflating (20) the balloon means within the duct for predetermined periods of time. An improved method of cholangiography is also provided and includes the steps of surgically incising the common bile duct of an anesthetized patient, inserting an inflatable hollow tube means (14) into the incised bile duct, inflating the tube means so as to seal the incision from the flow of liquid, injecting a radiopaque contrast agent through a hollow shaft means (11), communicating with the hollow tube means, into the bile duct, subjecting the injected bile duct to radiography whereby any stones therein can be detected, deflating the hollow tube means and removing any such stones as may be detected, repeating the steps of inflating, injecting, subjecting and deflating until the bile duct is free from stones and removing the inflatable tube means from the bile duct and the patient. The cholangiocath can be provided with a hypodermic syringe (40) in a sterile disposable package (75) to provide the user with a complete, sterile unit for the cholangiography procedure.

28 Claims, 12 Drawing Figures

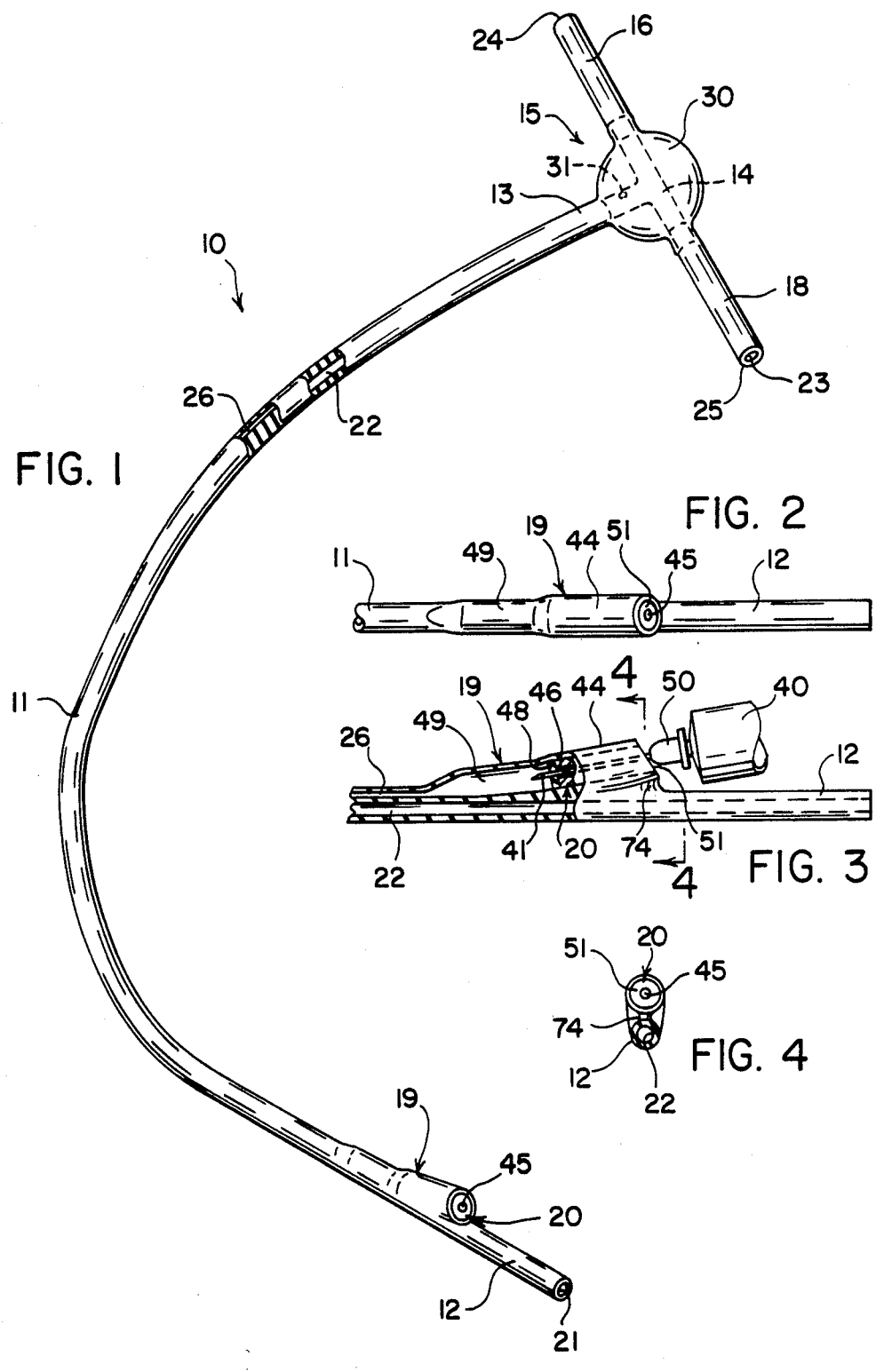

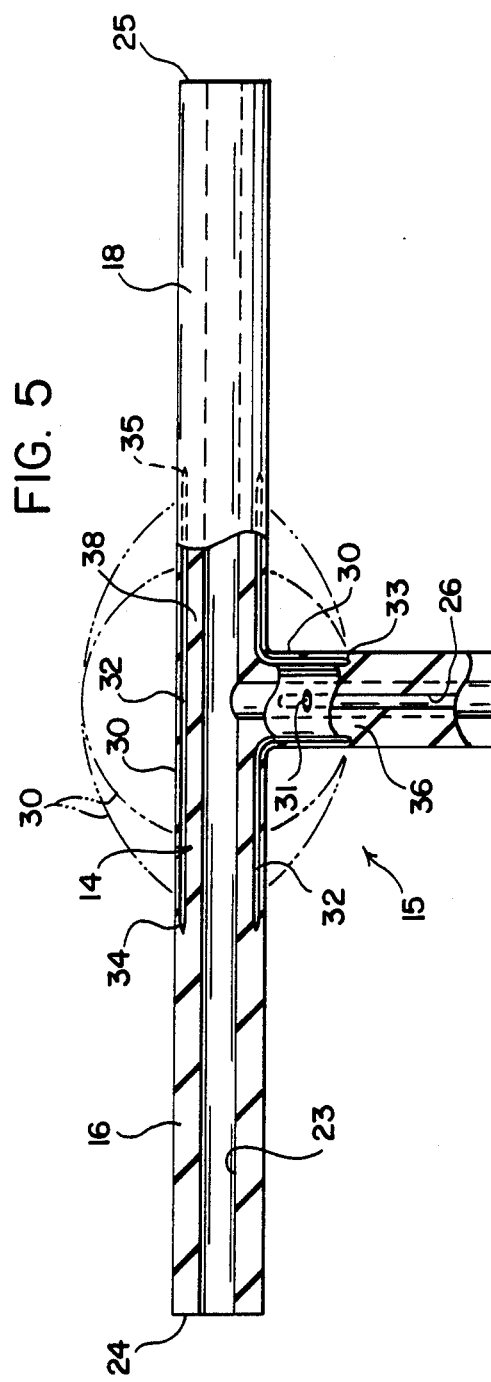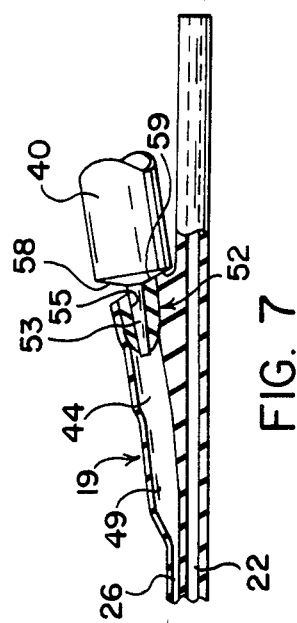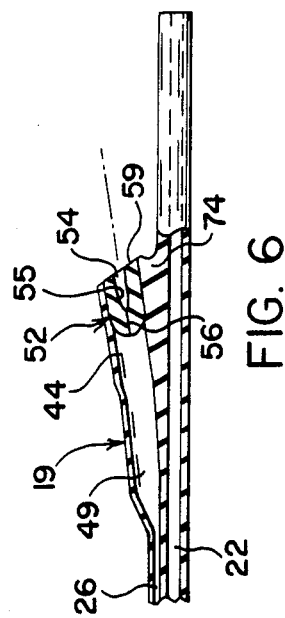

INFLATABLE CHOLANGIOCATH AND METHOD FOR CHOLANGIOGRAPHY THEREWITH

TECHNICAL FIELD

Patients suspected of having gallbladder disease are often subjected to a series of X-rays of the gallbladder and bile ducts (cholecystogram) to detect the presence of gallstones. This procedure usually requires the patient to swallow tablets containing a radiopaque dye. Other procedures including intravenous (I.V.) cholangiography and/or echograms can be utilized to detect or confirm the presence of gallstones.

Gallstones may lodge in the cystic duct or common bile duct of a patient causing great pain. Where the problem is a blocked duct, a ruptured gallbladder may result and, therefore, surgery may be necessary to remove either the stone or stones and/or the gallbladder (cholecystectomy). Approximately 500,000 cholecystectomies are performed annually in the United States. In about 30 percent of these cases, the patient will require exploration of the common bile duct (choledochotomy) for removal of gallstones.

BACKGROUND ART

The procedure whereby the common bile duct is explored following surgery is known as cholangiography whereby a device known as a T-tube is inserted into the common bile duct for the injection of a contrast material which will demonstrate the presence of gallstones. The T-tube is a hollow rubber tube that is shaped as the letter "T". The upper branch of the tee is actually inserted into the common bile duct and the long lower shaft extends out of the abdominal cavity and the patient to allow the surgeon to inject a radiopaque dye that will travel into the common bile duct.

The most troublesome problem in performing completion cholangiography, following exploration of the common bile duct, is the necessity of inserting and meticulously suturing the common bile duct around a T-tube before the injection of contrast material can be performed. Demonstration of retained stones necessitates removal of the secured T-tube and re-exploration of the common bile duct. Since the incidence of missed stones demonstrated by intraoperative cholangiography has been reported at 14 percent, this time consuming and often frustrating technical maneuver may have to be repeated several times before the common bile duct is cleared of stones.

Following completion cholangiography, the T-tube is finally sutured in the common bile duct and the shaft is passed through an incision in the abdominal wall allowing for drainage during the post-operative recovery period. A modified T-tube is known wherein an inflatable balloon is positioned some distance from the upper branch on the body of the main shaft. The balloon is inflated from outside of the patient and inflates just inside the abdominal wall thereby precluding inadvertent removal of the T-drain tube. Such a device was at least once listed in a supply catalogue of American Cystoscope Makers, Inc. but to the best of my knowledge is not presently used or even available.

Despite the number of cholecystectomies performed annually and the attendant problems that have been described, no one has provided a method whereby post-operative cholangiographies can be performed without suturing and removal of a T-tube in the common bile duct with possible repetitions. Similarly, a T-tube or other means that would obviate the suturing procedure has not been employed heretofore.

SUMMARY OF THE INVENTION

It is thereby an object of the present invention to provide an inflatable cholangiocath for cholangiographies.

It is another object to provide an inflatable cholangiocath which eliminates the need to suture, remove and resuture T-tubes in the common bile duct during identification and removal of common bile duct stones.

It is still another object to provide an inflatable cholangiocath which can be left in the common bile duct for the purpose of drainage and post-operative cholangiograms.

It is a further object to provide an inflatable cholangiocath of sufficient size to allow any possible post-operative radiologic extraction procedures to be performed.

It is yet another object of the present invention to provide in combination with a hypodermic syringe having a tip for the injection of air or other fluids, an inflatable cholangiocath.

It is yet another object of the present invention to provide a novel method for rapid roetgenographic assessment of the common bile duct which eliminates the steps of suturing, removing and resuturing the T-tube in the common bile duct.

These and other objects, together with the advantages thereof over known instruments and operative procedures, which shall become apparent from the specification which follows, are accomplished by the invention as hereinafter described and claimed.

The inflatable cholangiocath of the present invention includes an elongate shaft having a proximal and a distal end and a body wall, a second shaft carried at the distal end and having a body wall and left and right branches adapted to be inserted into an incised duct of a patient, a central drainage lumen extending from the proximal end, through the elongate shaft, and out the left and right branches, balloon means encompassing a portion of the distal end and the left and right branches, the balloon means being closed to the central drainage lumen and, means for selectively inflating and deflating the balloon means within the duct for predetermined periods of time.

An improved method of cholangiography is also provided and includes the steps of surgically incising the common bile duct of an anesthetized patient, inserting an inflatable hollow tube means into the incised bile duct, inflating a portion of the tube means so as to seal the incision from the flow of liquid therefrom, injecting a radiopaque contrast agent into the bile duct through a hollow shaft communicating with the hollow tube, subjecting the injected bile duct of roentgenography whereby any stones therein can be detected, deflating the hollow tube and removing any such stones as may be detected, repeating the steps of inflating, injecting, subjecting and deflating until the bile duct is free from stones and, removing the inflatable hollow tube means from the bile duct and the patient.

Lastly, the present invention provides in combination, a hypodermic syringe, having a tip for the injection of air or other fluids, and an inflatable cholangiocath as set forth herein. The overall combination of these components can be provided to the surgeon in a sterile, disposable package in order to insure that the proper components are selected for performing the method of cholangiography as set forth herein.

BRIEF DESCRIPTION OF THE DRAWINGS

FIG. 1 is a perspective view of the inflatable cholangiocath of the present invention in its inflated position and also depicting a hypodermic syringe with a needle for inflating the balloon;

FIG. 2 is a top plan view of the proximal end of the inflatable cholangiocath of the present invention;

FIG. 3 is a side elevation, partially in section of the proximal end of the inflatable cholangiocath of the present invention;

FIG. 4 is an end view, partially in section, taken substantially along the line 4—4 of FIG. 3;

FIG. 5 is an enlarged frontal elevation, partially in section, of the distal end of the inflatable cholangiocath of the present invention depicting the balloon in its uninflated stage;

FIG. 6 is a side elevation, partially in section and similar to FIG. 3, depicting a different valve;

FIG. 7 is a side elevation, partially in section and similar to FIG. 6, depicting the valve thereof and its interrelation with the tip of a hypodermic syringe in position for inflation or deflation;

PREFERRED MODE FOR CARRYING OUT THE INVENTION

Figure 8:
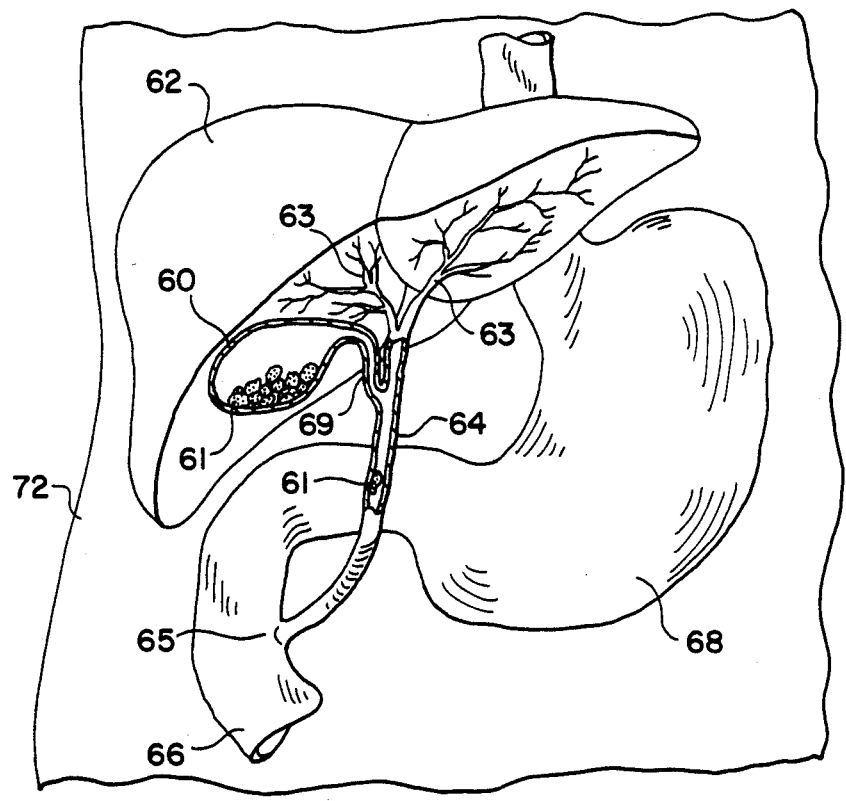
FIG. 8 schematically depicts the gallbladder and related viscera in a patient having gallstones.

The inflatable cholangiocath or tube means of the present invention is depicted generally by the numeral 10. It has an elongate shaft 11 which terminates at its proximal end 12 and is provided at its distal end 13 with a shorter shaft 14 which is carried perpendicular to the elongate shaft 11. The juncture of shafts 11 and 14 forms a letter T, indicated generally by the numeral 15. The shaft 14 includes a left and right branch, 16 and 18, respectively. A short distance from the proximal end 12, a side arm 19 integrally molded onto the shaft 11 which carries an inflation valve 20. The valve 20 provides a means through which air or a fluid, e.g., water or saline, can be injected as will be discussed hereinbelow.

At the very tip of proximal end 12 is an opening 21 which communicates with a central lumen 22 passing through the shaft 11. Lumen 22 also interconnects with a transverse lumen 23 in the shaft 14 opening at ends 24 and 25. In this manner, fluids can be passed into the ends 24 and 25, through the lumen 23 and out of the shaft 11 or, into the shaft 11 and out of the ends 24 and 25. A separate lumen 26 is provided adjacent to but separate from the lumen 22. It communicates with the inflation valve 20 and allows passage of air or a fluid into a balloon 30 provided at the T 15. Inflation lumen 26 terminates at 31 where an exit port is provided for entry of the inflating medium into a space or passageway 32 which is provided between the balloon 30 and the adjacent shafts of the T 15.

The balloon 30 extends a short distance along shaft 11 away from the T and the distal end 13, terminating at 33, and toward the left and right lateral branches 16 and 18, terminating at 34 and 35, respectively. As depicted in FIG. 2, the balloon 30 is separated from the body wall 36 of shaft 11 to the termination at 33 and is then continuous therewith. Similarly, the balloon 30 is separated from the body wall 38 of the shaft 14 and after the termination at 34 and 35, it is continuous therewith. During use, air or fluid is injected through the injection valve 20 causing the balloon 30 to inflate between the confines of ends 33, 34 and 35 forming a spherical bulge, depicted in FIG. 1 and in FIG. 2 in phantom.

If totally inflated, the balloon could be expanded more toward the football shape as is also depicted in phantom in FIG. 2. This occurs because the distance of points 34 and 35 from the T is greater than the distance to the point 33 on the shaft 11. The purpose of this design is to allow inflation to a maximum spherical diameter after which additional volume extends the balloon longitudinally which may be useful during inflation in a duct, such as the common bile duct, which will be discussed hereinbelow.

Generally, approximately 4 to 8 cc of volume will expand the balloon sufficiently which is to a diameter of at least three times the diameter of shafts 11 and 14. When deflated, the diameter of the balloon 30 encompassing the T 15 is substantially equal to the diameter of the shafts 11 and 14 where not encompassed by the balloon.

The valve 20 can be inflated and deflated directly with a hypodermic syringe 40 (FIG. 3) having a needle 41. Once inflated, balloon 30 remains distended until the air or fluid is withdrawn through the valve 20. The inflatable cholangiocath 10 is suitably manufactured of a latex rubber and can be made by a multiple dip method. The balloon 30, side arm 19 and inflation valve 20 can be provided according to known methods in the latex dipping art and, as such, does not form a part of the present invention. The latex can be natural rubber or a blend with silicone rubber employing the composition set forth in U.S. Pat. No. 4,242,287.

Briefly commenting on the method, inflatable catheters are usually made by a multiple dip process wherein successive layers are built up around mandrels. The balloon is formed by applying a coating of release material to the area where the balloon is required. Thus, in final dipping the rubber forming the balloon is contiguous with the shafts and is unitary with the previous layers where no coating is present and separate from the latter where the coating is present. As will be appreciated, the diameter of the shafts present within the balloon is somewhat less than where the balloon terminates and the shafts become solid which is clearly shown in FIG. 2.

With reference to FIGS. 1–4, and particularly the side arm 19, the valve 20 is carried in an outer segment or first chamber 44 of the latter terminating at the end of arm 19. The valve 20 provides an opening 45 and a guideway 46 for insertion of the needle 41. The guideway is preferably larger than the needle diameter and constructed of a material harder than the rubber of side arm 19 in order to insure that the needle is aligned with the inflation lumen 26 and is not misguided into the side arm 19 or shaft 11. At the end of the guideway 46, the valve 20 carries a rubber seal 48 that can be repeatedly punctured and will seal upon withdrawal of the needle. The inflation lumen 26 passes through the inner segment or second chamber 49 of the side arm 19 before being carried with the shaft 11.

It will be noted in FIG. 3 that the overall length of the needle 41 provided is selected so that the needle can extend through the guideway 46, first chamber 44 and rubber seal 48 and terminate within the second chamber 49 of side arm 19 when the hub 50 of the needle is against the face 51 of valve 20. Thus, there is no possibility of the needle being improperly thrust into or through the shaft 11. Once inflated properly by the syringe, the needle is withdrawn from the valve 20 and the balloon will remain inflated. To deflate, the needle is again inserted and will allow the air or fluid to be drawn quickly therethrough.

With reference to FIGS. 6 and 7, the description of another valve, 52, that can be employed in lieu of valve 20 will be presented. Valve 52 is a needleless valve and is designed for use with a standard Luer tip syringe 40. The tip 53 of such syringes normally engages the hub of a needle when the latter is employed. The valve 52 is also carried in the first chamber 44 of side arm 19 and has an opening 54 and guideway 55. Guideway 55 is constricted at its far end and forms a narrow slit 56 as depicted in FIG. 6. The valve is tightly fit within chamber 44 which has the effect of closing the slit 56 and inhibiting the passage of air or other fluid therethrough. It can also be cemented within the chamber as is true for the valve 20.

To use the valve 52, the tip 53 of syringe 40 is inserted into the guideway 55 until the syringe bottom 58 contacts the face 59 of valve 52. In this position, depicted in FIG. 7, the tip 53 has just entered into the second chamber 49, opening the slit 56 sufficiently for air to be injected therethrough and forward into the balloon 30. When the tip and syringe are withdrawn, the constriction of chamber 44 seals the slit and likewise the air within balloon 30. When the balloon is to be deflated, the tip is again inserted until it opens the slit whereupon the air is released into the syringe.

Surgeons may prefer the needleless valve 52 inasmuch as it avoids possibility of misdirecting the needle 41 in valve 20, necessitating a repeated attempt. Nevertheless, it is to be understood that the cholangiocath of the present invention is equally operable with either valve for use in cholangiography.

Figure 9:
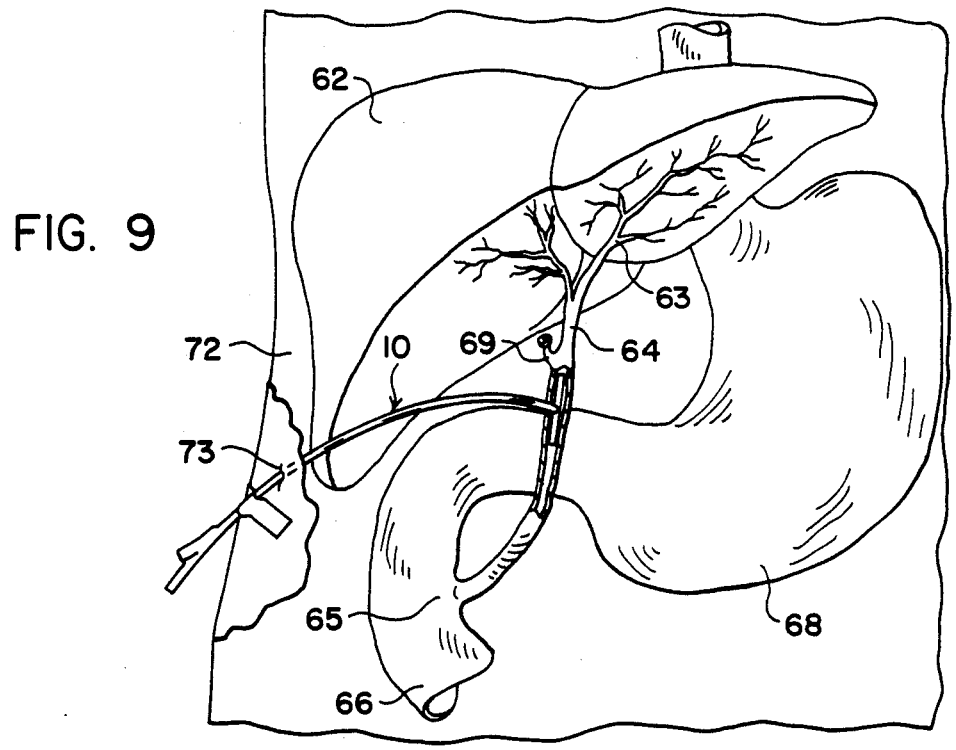
FIG. 9 is similar to FIG. 8 and schematically depicts the viscera in a patient following removal of the gallbladder and a gallstone from within the common bile duct and which depicts the use of the inflatable cholangiocath of the present invention.

With reference next to FIGS. 8 and 9, a quick summary of a typical surgical procedure requiring the use of the T-tube 10 shall be described. In FIG. 8 a diseased gallbladder 60 is depicted having a plurality of gallstones 61. The gallbladder 60 lies beneath the liver 62 and stores excess bile produced in the latter organ. Bile is employed to air in the digestion of fats and passes from the liver via the hepatic ducts 63 into the common bile duct 64 and into the duodenum 65 of the small intestine 66 which receives food from the stomach 68. Excess bile is stored in the gallbladder 60 and exits therefrom via the cystic duct 69 into the common duct 64. A separate gallstone 61 is depicted as lodged in the common bile duct 64 which is often encountered during surgery.

Figure 10:
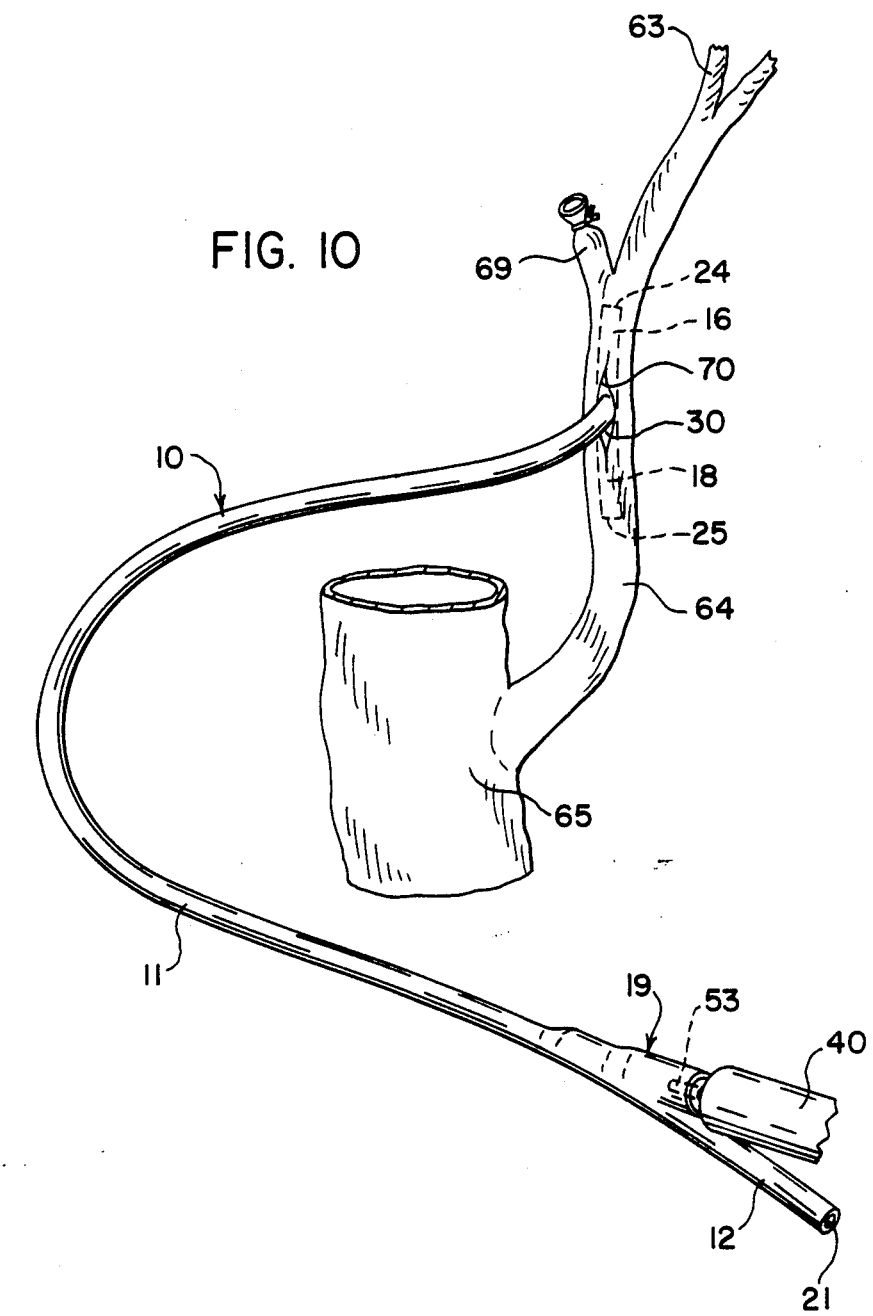
FIG. 10 is an enlarged area depicting the common bile duct and the inflatable cholangiocath of the present invention in position prior to inflation.

In FIG. 9 the gallbladder 60 has been removed, the cystic duct 69 has been tied off and a choledochotomy or surgical incision of the common bile duct 64 has been made. The incision, at 70 (FIGS. 10 and 11), is made to remove the lodged gallstone 61 and also to allow exploration of the common duct 64 for additional gallstones. Following exploration of the common bile duct 64, the inflatable cholangiocath 10 is inserted into the choledochotomy as depicted in FIG. 10.

Figure 11:
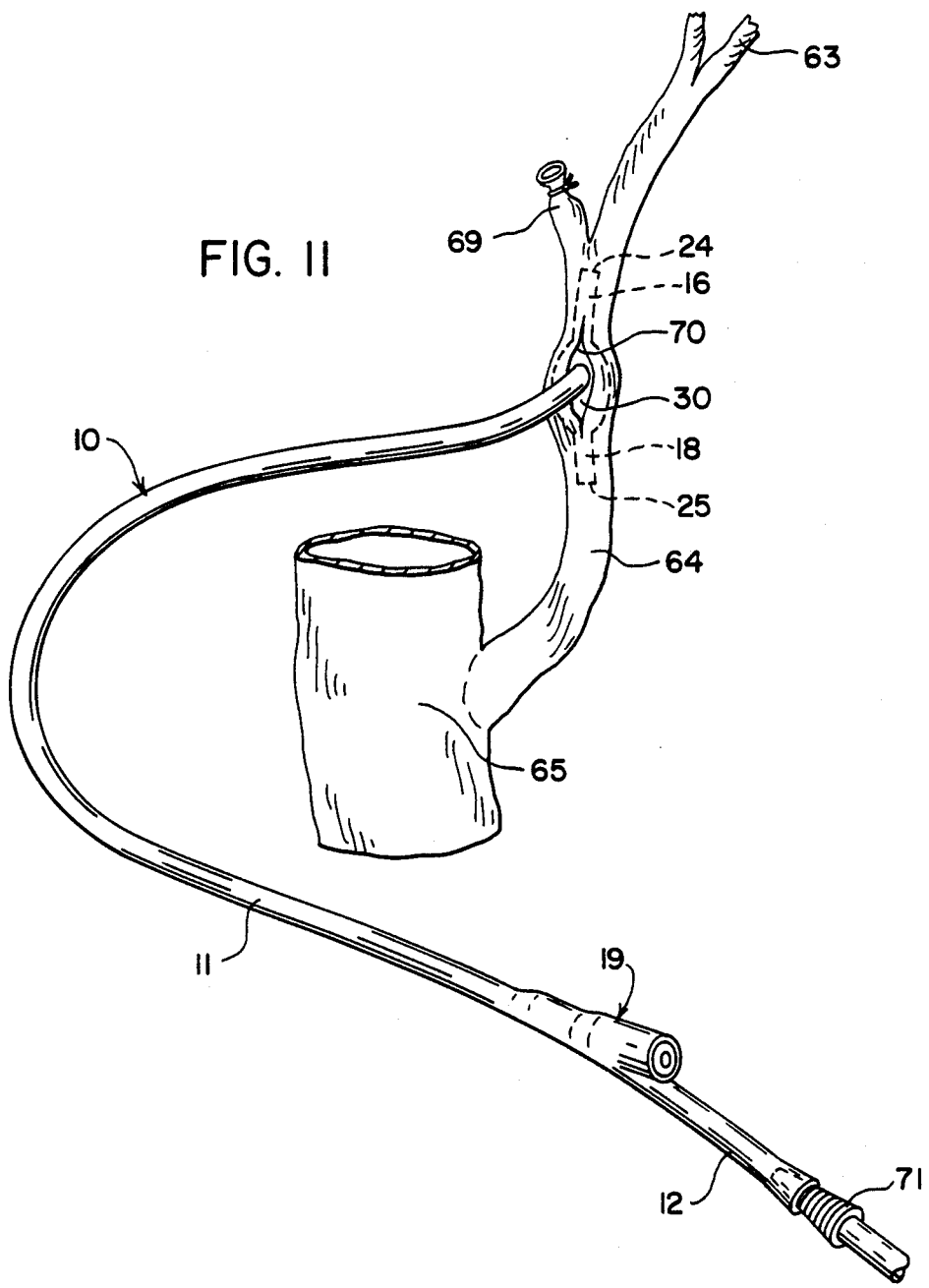
FIG. 11 is an enlarged area depicting the common bile duct and the inflatable cholangiocath of the present invention inflated therein.

The balloon 30 is next inflated with 4 to 8 milliliters of air or water with the syringe 40 via valve 20 or 52, whichever is available, and a fluid tight system or seal is created, as depicted in FIG. 11. A cholangiogram is then performed by injecting 5 to 10 milliliters of a diluted 50 percent contrast agent (16 percent final concentration) with a separate syringe or similar apparatus 71 inserted into the proximal end 12 of shaft 11 which passes the agent through the cholangiocath ends 24 and 25 and into duct 64. If stones are detected in the duct, the inflatable balloon is easily and quickly removed by simply removing the air or water from the balloon and the stones removed from the common bile duct. If no stones are identified and contrast material flows freely into the duodenum, the balloon is deflated and the inflatable cholangiocath 10 is sutured securely in place.

At this point of the procedure, the inflatable cholangiocath of the present invention functions as T-tubes presently employed in the art. That is, bile drainage is collected and measured daily by attaching a bag or other collection device to the proximal end 12, after removal of the syringe 40. Inasmuch as neither the balloon 30 nor the shaft 14 occludes the common bile duct 64, bile can also pass from the liver through the lumen 23 and into the duodenum. The cholangiocath 10 is pased through the abdominal wall 72 at a separate smaller incision 73 (FIG. 7) and is generally allowed to remain in for 8–10 days, for a last routine cholangiogram. When the surgeon has determined that no more stones are present or that other problems exist, the cholangiocath 10 is simply pulled out of the duct 64 and through the small abdominal incision 73.

The cholangiocath 10 is preferably constructed of a suitable size such as 14F (0.50 cm) to allow any possible post-operative radiologic extraction procedures to be performed while it is in position. As stated hereinabove, it can be manufactured according to known methods in the art which includes techniques for forming the balloon. The cholangiocath 10 is intended to be disposable although reuse could be possible by employing suitable sterilization procedures.

The design of the cholangiocath 10 also aids the surgeon in passing the shaft 11 through the incision 73. As depicted in FIGS. 2–4, the face 51 of valve 20 is cut oblique to the shaft 11, providing a sloping surface to the incision as it is pulled therethrough. The first chamber 44 of side arm 19 is also angularly disposed with respect to the shaft 11 via web 74 which elevates a portion of the chamber 44 away from the shaft 11. The remainder of chamber 44 and the second chamber 49 are integrally molded into the body wall 36 of the shaft 11. The design of the first and second chambers and web 74 is generally the same when valve 52 is substituted for valve 20. Of course, the rubber seal 48 employed in conjunction with valve 20 is not present with valve 52.

Inasmuch as the shaft and side arm therefore have a minimal, compact heighth, the incision 73 need not be any longer which is desirable to both the surgeon and the patient. The distance that the shaft 11 extends beyond the side arm 19 also provides a convenient area for gripping when the radiopaque dye injecting means is inserted therein and later when the shaft is to be passed through the incision 73. One useful procedure may be for the surgeon to pass the tip of a hemostat through the incision 73 and into the patient, grip the shaft 11 and pull it and the side arm therethrough.

The inflatable cholangiocath 10 was successfully employed in 18 patients without any complications or injury to the common bile duct. In three patients more than one cholangiogram with exploration had to be done in order to free the common bile duct of stones. The roentgenographic delineation of the common bile duct using the inflatable cholangiocath 10 has been as good as that utilizing the conventional T-tube. No evidence of contrast leak was evident with the use of the tube. In none of the eighteen patients were retained stones found on the routine postoperative cholangiograms. Removal of the inflatable cholangiocath before the patients were discharged was without incident.

While the inflatable cholangiocath of the present invention can be inflated with substantially any hypodermic syringe, having a Luer tip, available in the operating room, in the interest of providing the surgeon with a complete, sterile unit for the procedure, it is within the scope of the invention that the cholangiocath 10 be packaged with its own syringe.

Figure 12:
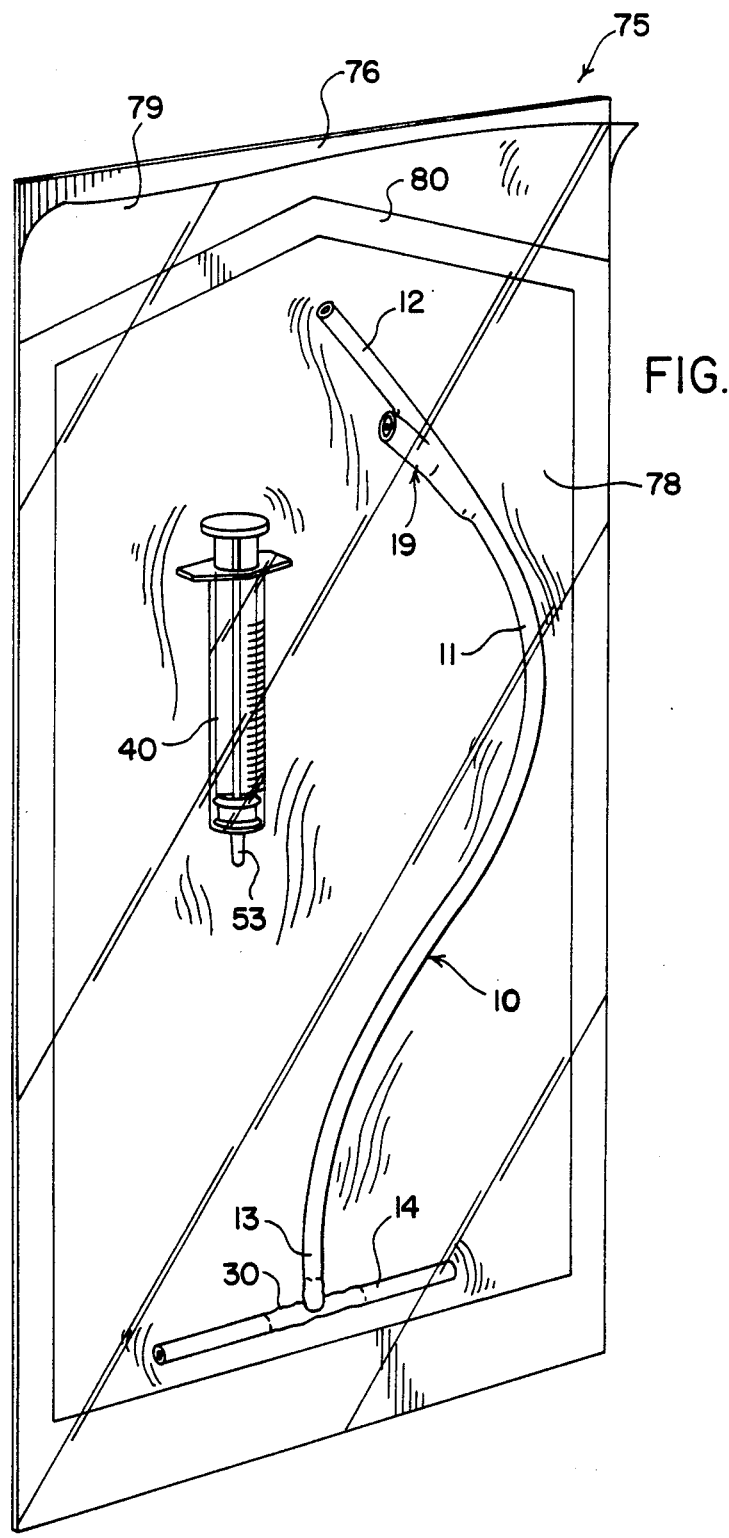
FIG. 12 is a perspective view of the inflatable cholangiocath of the present invention in combination with a hypodermic syringe in a sterile, disposable package as a unit to be provided to a surgeon to aid in performing the method of cholangiography set forth hereinbelow.

With reference to FIG. 12, such a proposal is depicted which includes a sealed, disposable packaging envelope 75, a cholangiocath 10 according to the present invention, and a hypodermic syringe 40. Besides eliminating the possibility that a suitable syringe might not be available at the required moment, the provision of a separate syringe insures that the balloon 30 will be correctly operated and at the instant the surgeon desires. When the cholangiocath carries the valve 20, a separate needle (not shown) would also be provided in the package 75, again assuring the presence of a complete unit for the procedure and obviating the need to search for a needle or the risk of employing one of improper length.

The package 75 may comprise paper or other suitable backing material 76. A clear plastic cover 78 is bonded to the backing 76 forming a closed package, the contents of which are visible. The package 75 is opened for use by pulling the upper flap 79 of cover 78 from the backing material 76. The bonding can comprise a pressure-sensitive adhesive layer, depicted by the numeral 80, which allows the cover 78 to separate from the backing material 76 to a sufficient degree for the syringe and cholangiocath to be removed therefrom. As will be appreciated, instructions and other printed information can be employed on the face of the backing material and will be visible through the cover 78.

Thus, it can be seen that the disclosed invention carries out the objects set forth hereinabove. By employing an inflatable cholangiocath as described herein for cholangiography immediately following a cholecystectomy, the time and trauma to the patient for subsequent detection and removal of stones from the common bile duct can be greatly reduced. This results in a simplification in the surgical procedure, as is reflected in the method of the present invention. As will be apparent to those skilled in the art, the inflatable cholangiocath of the present invention could be employed in other surgical procedures such as where a duct or other passageway or cavity required an exchange of fluids intra and extra corporally, particularly for roentgenographic analysis. Any such variations including but not limited to size of the inflatable cholangiocath, materials employed or steps in the method of use can be determined without departing from the spirit of the invention herein disclosed and described. Moreover, the scope of the invention shall include all modifications and variations that fall within the scope of the attached claims.

I claim:

1. An inflatable cholangiocath for use in roentgenography comprising:
   elongate shaft means having a proximal and a distal end and a body wall;
   second shaft means of substantially equal diameter to said elongate shaft means and carried at said distal end thereof having a body wall and left and right branches adapted to be inserted into an incised duct of a patient;
   a central drainage lumen extending from said proximal end, through said elongate shaft, and out said left and right branches;
   balloon means encompassing a portion of said distal end and said left and right branches, said balloon means being closed to said central drainage lumen; and
   means for selectively inflating and deflating said balloon means within the duct for predetermined periods of time;
   wherein said balloon means is generally spherical when inflated;
   is inflatable to a diameter of at least three times the diameter of said elongate shaft and second shaft means;
   conforms to the diameter of said elongate shaft and second shaft means when deflated and
   can be removed from the common bile duct and the patient without surgery.

2. An inflatable cholangiocath, as set forth in claim 1, wherein said means for selectively inflating and deflating comprises:
   valve means for the injection and removal of air or other fluids with respect to said balloon means;
   second lumen means extending from said valve means through said elongate shaft adjacent to and separate from said drainage lumen and open to said balloon means; and
   first chamber means carried by said elongate shaft means and carrying said valve means.

3. An inflatable cholangiocath, as set forth in claim 2, said means for selectively inflating and deflating further having second chamber means carried by said elongate shaft means, contiguous with said first chamber means and providing a communication between said valve means and said second lumen means.

4. An inflatable cholangiocath, as set forth in claim 3, further having:
   web means interposed between a portion of said first chamber means and said elongate shaft means thereby angularly disposing said valve means from the longitudinal axis of said elongate shaft;
   said valve means having an oblique exterior face forming an obtuse angle with said elongate shaft means; and
   the remaining portion of said first chamber means and all of said second chamber means being integrally molded into said body wall of said elongate shaft.

5. An inflatable cholangiocath, as set forth in claim 4, wherein said proximal end extends below said valve means to receive an injection from an instrument providing a contrast medium.

6. An inflatable cholangiocath, as set forth in claim 1, wherein said second shaft means is shorter than said elongate shaft means and said left and right branches are generally perpendicular to said elongate shaft means.

7. An inflatable cholangiocath, as set forth in claim 1, wherein said elongate shaft and second shaft means are of substantially equal diameter.

8. An improved method of cholangiography including the steps of:
    surgically incising the common bile duct of an anesthetized patient;
    inserting an inflatable hollow tube means into said incised bile duct;
    injecting a radiopaque contrast agent into said bile duct through a hollow shaft means communicating with said hollow tube means;
    subjecting said injected bile duct to roentgenography whereby any stones therein can be detected;
    deflating said hollow tube means, removing said hollow tube means from said bile duct and removing any such stones as may be detected;
    repeating said steps of inserting, inflating, injecting, subjecting and deflating until said bile duct is free from stones; and
    removing said inflatable tube means from said bile duct and the patient after all of the stones have been removed;
    the improvement comprising:
    inflating a portion of said tube means, after said step of inserting, so as to seal said incision with respect to the flow of liquid therefrom, said seal being created at the site of said incision, whereby suturing said hollow tube means into said bile duct before said step of injecting is obviated.

9. An improved method, as set forth in claim 8, including the further step of:
    securing said inflatable tube means within said bile duct between said last step of deflating and said step of removing to provide a drain out of the patient following surgery.

10. An improved method, as set forth in claim 8, wherein said inflatable hollow tube means comprises:
    left and right branches carried at one end of said hollow shaft, a central drainage lumen being common to said hollow shaft and said inflatable hollow tube means; and
    balloon means emcompassing a portion of said hollow shaft and said left and right branches, said balloon means being closed to said central lumen.

11. An improved method, as set forth in claim 10, wherein said hollow shaft is provided with means for selectively inflating and deflating said balloon means and said means comprises:
    valve means for the injection and removal of air or other fluids with respect to said balloon means;
    second lumen means extending from said valve means through said hollow shaft adjacent to and separate from said central lumen and open to said balloon means; and
    first chamber means carried by said hollow shaft means and carrying said valve means.

12. An improved method, as set forth in claim 11, said means for selectively inflating and deflating further having second chamber means carried by said hollow shaft, contiguous with said first chamber means and providing a communication between said valve means and said second lumen means.

13. An improved method, as set forth in claim 12, wherein a portion of said hollow shaft extends below said valve means to receive an injection from an instrument providing a contrast medium.

14. An improved method, as set forth in claim 10, wherein said inflatable hollow tube means is shorter than said hollow shaft and said left and right branches are generally perpendicular to said hollow shaft.

15. An improved method, as set forth in claim 10, wherein said inflatable hollow tube means and hollow shaft are of substantially equal diameter.

16. An improved method, as set forth in claim 15, wherein said balloon means is generally spherical when inflated and is inflatable to a diameter of at least three times the diameter of said inflatable hollow tube means and hollow shaft.

17. An improved method, as set forth in claim 10, wherein said balloon means conforms to the diameter of said hollow shaft and inflatable hollow tube means when deflated and can be removed from the common bile duct and the patient without surgery.

18. In combination with a hypodermic syringe having a tip for the injection of air or other fluids, an inflatable cholangiocath for use in roentgenography comprising:
    elongate shaft means having a proximal and a distal end and a body wall;
    second shaft means carried at said distal end having a body wall and left and right branches adapted to be inserted into an incised duct of a patient;
    a central drainage lumen extending from said proximal end, through an elongate shaft, and out said left and right branches;
    balloon means encompassing a portion of said distal end and said left and right branches, said balloon means being closed to said central drainage lumen; and
    means for selectively inflating and deflating said balloon means within the duct for predetermined periods of time;
    wherein said balloon means conforms to the diameter of said elongate shaft and second shaft means when deflated and can be removed from the common bile duct and the patient without surgery.

19. In combination with a hypodermic syringe, an inflatable cholangiocath as defined in claim 18, wherein said means for selectively inflating and deflating comprises:
    valve means for the injection and removal of air or other fluids with respect to said balloon means;
    second lumen means extending from said valve means through said elongate shaft adjacent to and separate from said drainage lumen and open to said balloon means; and
    first chamber means carried by said elongate shaft means and carrying said valve means.

20. In combination with a hypodermic syringe, an inflatable cholangiocath as defined in claim 19, said means for selectively inflating and deflating further having second chamber means carried by said elongate shaft means, contiguous with said first chamber means and providing a communication between said valve means and said second lumen means.

21. In combination with a hypodermic syringe, an inflatable cholangiocath as defined in claim 20, further having:
    web means interposed between a portion of said first chamber means and said elongate shaft means thereby angularly disposing said valve means from the longitudinal axis of said elongate shaft;

said valve means having an oblique exterior face forming an obtuse angle with said elongate shaft means; and the remaining portion of said first chamber means and all of said second chamber means being integrally molded into said body wall of said elongate shaft.

22. In combination with a hypodermic syringe, an inflatable cholangiocath as defined in claim 21, wherein said proximal end extends below said valve means to receive an injection from an instrument providing a contrast medium.

23. In combination with a hypodermic syringe, an inflatable cholangiocath as defined in claim 20, wherein said syringe and inflatable cholangiocath are provided in a sterile disposable package.

24. In combination with a hypodermic syringe, an inflatable cholangiocath as defined in claim 23, wherein said package further carries a hollow needle engageable with said syringe tip and with said means for selectively inflating and deflating.

25. In combination with a hypodermic syringe, an inflatable cholangiocath as defined in claim 24, wherein the length of said needle is sufficient to pass through said valve and said first chamber means and extends into said second chamber means.

26. In combination with a hypodermic syringe, an inflatable cholangiocath as defined in claim 18, wherein said second shaft means is shorter than said elongate shaft means and said left and right branches are generally perpendicular to said elongate shaft means.

27. In combination with a hypodermic syringe, an inflatable cholangiocath as defined in claim 18, wherein said elongate shaft and second shaft means are of substantially equal diameter.

28. In combination with a hypodermic syringe, an inflatable cholangiocath as defined in claim 27, wherein said balloon means is generally spherical when inflated and is inflatable to a diameter of at least three times the diameter of said elongate shaft and second shaft means.

* * * * *